United States Patent [19]

Kreuzer

[11] 4,048,499

[45] Sept. 13, 1977

[54] INFRARED ABSORPTION SPECTROSCOPY OF LIQUIDS EMPLOYING A THERMAL DETECTOR

[75] Inventor: Lloyd B. Kreuzer, San Francisco, Calif.

[73] Assignee: Diax Corporation, Sunnyvale, Calif.

[21] Appl. No.: 551,270

[22] Filed: Feb. 20, 1975

[51] Int. Cl.² .............................................. G01J 1/00
[52] U.S. Cl. .................................... 250/344; 250/346
[58] Field of Search ....................... 250/393, 346, 344; 350/97

[56] References Cited

U.S. PATENT DOCUMENTS

| 2,386,830 | 10/1945 | Wright | 250/346 |
|---|---|---|---|
| 2,386,831 | 10/1945 | Wright | 250/346 |
| 2,737,591 | 3/1956 | Wright et al. | 250/346 |
| 2,939,953 | 6/1960 | Parsons et al. | 250/346 |
| 3,560,735 | 2/1971 | Strange et al. | 250/343 |
| 3,560,736 | 2/1971 | Billetdeaux et al. | 250/343 |
| 3,560,738 | 2/1971 | Strange | 250/343 |
| 3,820,901 | 6/1974 | Krenzer | 350/97 |
| 3,851,176 | 11/1974 | Jeunehomme et al. | 250/343 |

Primary Examiner—Alfred E. Smith
Assistant Examiner—Bruce C. Anderson
Attorney, Agent, or Firm—Lowhurst & Aine

[57] ABSTRACT

In an infrared laser absorption spectrometer, an infrared laser beam of predetermined wavelength, in the infrared absorption spectrum, is beamed into a liquid sample under analysis. Components of the liquid sample absorb energy from the infrared beam, as a function of the infrared wavelength of the beam, to produce heating of the liquid. A thermal detector is disposed in heat exchanging relation with the liquid sample for detecting the heating effect in the liquid due to absorption of the infrared radiation. This detection scheme is particularly useful for monitoring the effluent of a liquid chromatograph as it provides specific detection.

14 Claims, 2 Drawing Figures

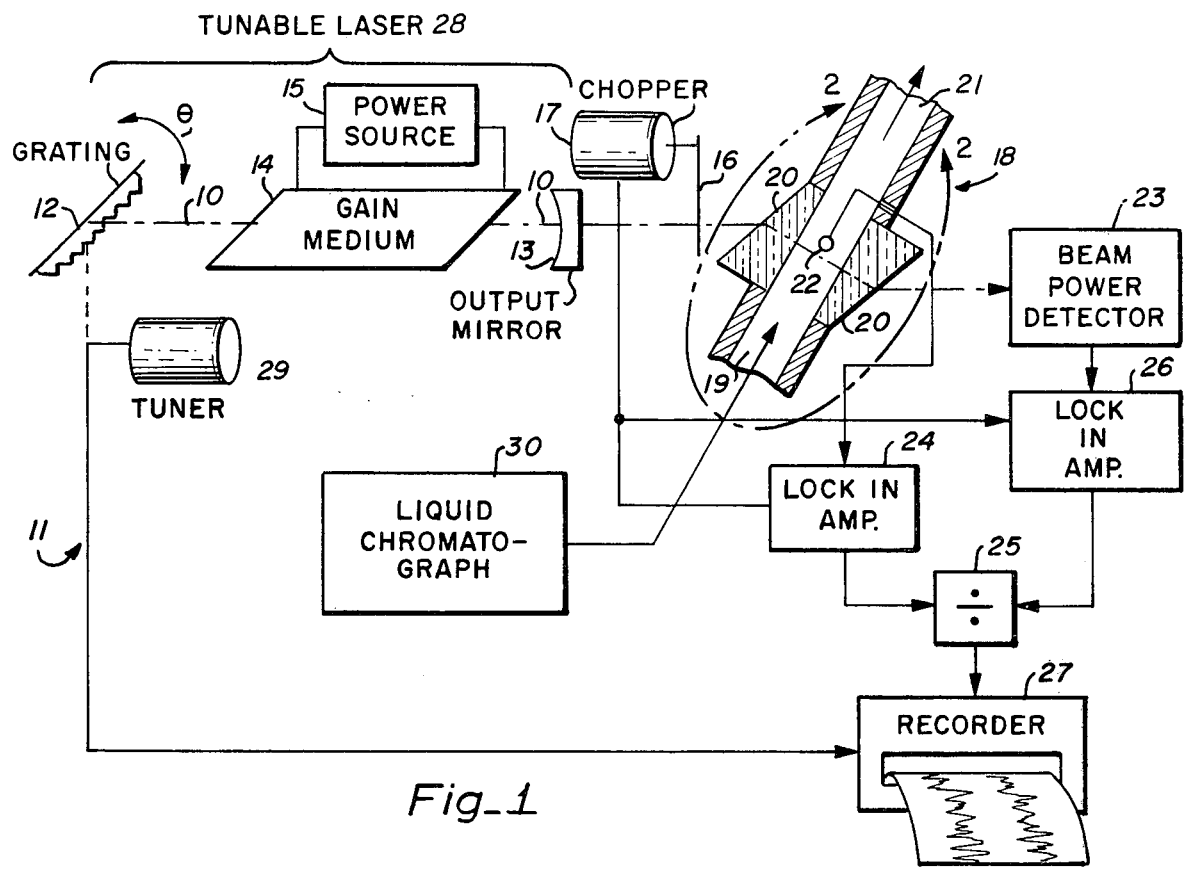
Fig_1
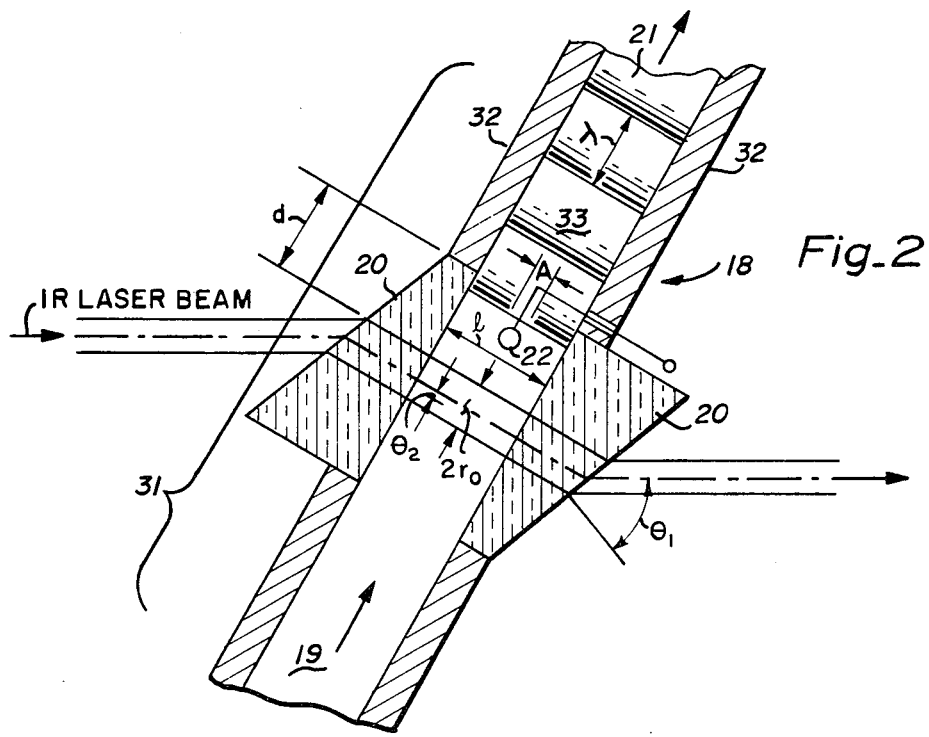
Fig_2

INFRARED ABSORPTION SPECTROSCOPY OF LIQUIDS EMPLOYING A THERMAL DETECTOR

BACKGROUND OF THE INVENTION

The present invention relates in general to laser absorption spectroscopy and, more particularly, to such spectroscopy wherein absorption of infrared energy from a laser beam by a liquid sample under analysis is monitored by a thermal detector coupled in energy exchanging relation with the sample for detecting energy absorption as a function of the wavelength of the laser beam applied to the sample

DESCRIPTION OF THE PRIOR ART

Heretofore, infrared laser absorption spectroscopy has employed an optoacoustic sample detection cell for analyzing gaseous samples and, in particular, for detecting certain pollutants in the air to concentration levels as low as parts per billion. Such a laser spectrometer is disclosed in: U.S. Pat. No. 3,820,901 issued June 28, 1974; in an article titled "Laser Optoacoustic Spectroscopy: A New Technique of Gas Analysis" appearing in *Analytical Chemistry,* Vol. 46, No. 2, of February 1974, pages 239–244; in *Science,* Vol. 177, pages 347–349 of July 1972 in an article titled "Air Pollution: Sensitive Detection of Ten Pollutant Gases by Carbon Monoxide and Carbon Dioxide Lasers"; and in U.S. Pat. No. 3,659,492, issued May 2, 1972.

In these prior art laser absorption spectrometers, the laser, which is preferably a relatively high power output carbon dioxide or carbon monoxide laser, produces an output laser beam which is tunable to select wavelengths within a band of infrared wavelengths of interest, i.e., in the band of wavelengths over which certain gaseous sample constituents are known to have infrared absorption spectra. The laser output beam is directed through an optoacoustic cell containing the gaseous material to be analyzed. A sensitive microphone is coupled to the gaseous sample inside the sample cell.

The laser beam is chopped at a certain chopping frequency, as of 25 Hertz, to produce a corresponding modulation of the absorption of the laser beam energy by the sample of gas under analysis. Absorption of energy from the laser beam by the gas produces heating thereof which results in generating an acoustic wave which is detected by the microphone. The detected signal is processed to produce an output signal as a function of the wavelength of the infrared energy of the tunable laser beam to derive absorption spectral data concerning the sample under analysis.

In liquid chromatography, where it is desired to detect sample constituents in a liquid effluent stream of a liquid chromatograph, such liquid constituents have heretofore been detected by a number of different techniques. In one prior technique, a beam of optical radiation has been directed onto the liquid effluent stream and the deflection angle measured to derive an output proportional to the index of refraction which varies from one liquid constituent to the next. This technique lacks the desired degree of specificity.

In another detection scheme for use in monitoring the effluent stream of liquid chromatograph a thermal detector has been employed to detect the absorption heat of formation of various liquid constituents absorbed on the surface of the detector. This type of detector offers improvements in specificity but it is desired to increase the degree of specificity to something more nearly akin to that obtained for an optoacoustic sample detection cell used in an infrared laser absorption spectrometer of the type previously described herein.

SUMMARY OF THE PRESENT INVENTION

The principal object of the present invention is the provision of an improved infrared absorption spectrometer for detecting and analyzing liquid samples.

In one feature of the present invention, the liquid sample to be analyzed is interposed in a beam of infrared radiation and a thermal detector means is disposed in heat exchanging relation with the liquid sample for detecting the heating effect in the liquid sample due to the absorption of infrared radiation by the sample from the applied beam of infrared radiation.

In another feature of the present invention, the beam of infrared radiation to be absorbed by the liquid sample is coherent radiation and a thermal detector is disposed in heat exchanging relation with the liquid sample for detection of the heating effect due to the absorption of infrared radiation by the sample.

In another feature of the present invention, the liquid sample is caused to flow and the thermal detector is disposed in the liquid sample downstream of the incident beam of infrared radiation so that the heating effect in the liquid sample is carried from the infrared beam path to the thermal detector.

In another feature of the present invention the infrared beam is focused to a radius in the liquid to be detected to less than one-half the modulated thermal wavelength $\lambda$ where $\lambda = V/f_0$ where $V$ is the liquid flow rate in centimeters per second and $f_0$ is the beam modulation frequency.

In another feature of the present invention, the major cross-sectional dimension of the thermal detector, which faces upstream of the direction of liquid flow, is dimensioned less than $\lambda/2$ where $\lambda$ is the modulation thermal wavelength, above defined.

In another feature of the present invention the distance from the thermal detector to the outer diameter of the infrared beam path in the beam detector cell is less than $V^3/\omega^2\alpha$ where $V$ is the velocity of the liquid stream in the detector cell, $\omega$ is the IR beam modulation frequency in radians, and $\alpha = K/PC$ where $K$ is the thermal conductivity, $P$ is the density and $C$ is the specific heat, respectively, of the liquid sample.

In another feature of the present invention, the thermal detector cell includes an infrared permeable window portion through which the beam of infrared radiation is directed into the liquid sample, and wherein the window has one face interfacing with the liquid and a second face interfacing with the medium surrounding the cell and wherein both faces of the window are disposed at Brewster angle to the laser beam in the respective medium.

Other features and advantages of the present invention will become apparent upon a perusal of the following specification taken in connection with the accompanying drawings wherein:

BRIEF DESCRIPTION OF THE DRAWINGS

FIG. 1 is a schematic line diagram, partly in block diagram form, of a laser spectrometer incorporating features of the present invention; and FIG. 2 is an enlarged detail view of a portion of the structure of FIG. 1 delineated by line 2—2.

DESCRIPTION OF THE PREFERRED EMBODIMENTS

Referring now to FIG. 1 there is shown a laser spectrometer 11 incorporating features of the present invention. Briefly, the spectrometer 11 includes an optical cavity resonator defined by the optical beam path between a diffraction grating 12 (wavelength selector) and a partially transmissive output mirror 13. An envelope 14, having Brewster windows at opposite ends and containing a conventional gaseous laser gain medium, such as carbon monoxide, carbon dioxide, or helium-neon mixture, is interposed along the optical resonator path 10 between the grating 12 and the output mirror 13. The gain medium is excited by a suitable electrical discharge to provide coherent stimulated emission of radiation at a resonant optical wavelength of the optical cavity resonator. Power is supplied from a power supply 15 to the gain medium to sustain the electrical discharge and laser action.

The output mirror 13 is an output coupler for the laser beam and its reflectivity is preferably matched to the gain of each laser line to gain maximum output power for each laser line (wavelength). The output laser beam is modulated by means of a rotatable perforated chopper disc 16 driven by a motor 17. A sample cell 18 is disposed in the modulated or chopped laser beam path. A liquid sample to be analyzed is caused to flow through the sample cell 18 via inlet and outlet passageways 19 and 21.

A thermal detector 22, such as a thermistor, is disposed in thermal energy exchanging relation with the liquid within the sample cell 18 and preferably is disposed downstream of the beam path through the cell 18. A beam power detector 23 is disposed at the terminal end of the laser beam path for monitoring the beam power incident thereon. The sample cell 18 includes a pair of Brewster angle windows 20 transmissive to the infrared wavelength of the laser beam to allow the laser beam to pass through the sample cell 18.

In operation, each pulse of the chopped laser beam, which is incident on the liquid sample at a wavelength corresponding to an absorption line of the liquid sample material, produces absorption of power from the laser beam and consequent heating of the liquid sample within the cell 18. The heating effect, caused by absorption of the laser beam by constituents of the liquid sample, is modulated due to the modulation of the laser beam at the chopper frequency thus producing thermal waves of a frequency corresponding to the chopper frequency and of a wavelength dependent upon the velocity of the liquid flow stream in the sample cell 18.

The thermal waves are picked up by the thermal detector 22 and fed to one input of a lock-in amplifier 24 for amplification and synchronous detection against a sample of the chopped frequency, as of 10 Hertz, derived from chopper 17. The amplified and detected output signal, which is a measure of the absorbance of the laser beam by the sample, is fed to one input of a divider 25 for division by a second signal derived from a second lock-in amplifier 25 which similarly lock-in amplifies and detects the beam power detected by the beam power detector 23. The second lock-in amplifier 26 also receives a reference signal from the chopper 17.

The output of the divider 25 corresponds to a sample absorption signal normalized to the beam power and this signal is recorded in a recorder 27 as a function of the wavelength of the tunable laser 28 as tuned by a tuner motor 29 which tunes the laser 28 by changing the angle $\theta$ of the diffraction grating 12. Thus, the recorder 27 records on absorption spectrum of the sample, such absorption spectrum being normalized to the beam power. In a typical example, the liquid stream to be analyzed is the effluent stream of a liquid chromatograph 30, whereby a sensitive and specific detector is provided for a liquid chromatograph.

Referring now to FIG. 2 there is shown, in greater detail, the liquid detector cell 18 of the present invention. The liquid detector cell 18 includes a length of rectangular tubing 31 having a pair of mutually opposed broad sidewalls 32 spaced apart by a pair of narrow sidewalls 33. A pair of Brewster angle infrared transmissive windows 20 are sealed into the broad sidewalls 32 of the tubing 31. The window transition section is arranged to provide laminar flow for the liquid sample through the detector cell 18 from a region upstream of the windows 20 to a region downstream of the detector 22.

The cell path length $l$ is preferably short to reduce the effect of solvent absorption in the liquid sample material. Temperature variations with time are attenuated by $1/e$ over a skin depth of $\delta = \sqrt{2\alpha/\omega}$ where $\omega$ is the thermal modulation frequency and $\alpha = K/PC$ where $K$ is thermal conductivity, $P$ is density and $C$ is specific heat of the liquid. It is desirable to locate the temperature sensor 22 close to the beam path and to make the thermal response time of the detector relatively short compared to the modulation frequency superimposed on the laser beam by the chopper. For many liquids $K = 50 \times 10^{-5}$ (Cal./cm$^2$ sec) ($^\circ$ C/cm)

$$C = 0.5 \frac{Cal}{g^\circ C.}$$

$$P = 1g/cm^3$$

$\alpha$ is approximately $10^{-3}$ for most liquids. Substituting into the above expressions for a modulation frequency of 10 Hertz, $\delta$ is approximately equal to $6 \times 10^{116\,3}$ cm.

What this means is that the detector should be located near the area where the beam is absorbed and preferably the liquid should flow from the laser beam absorption region to the detector. Typical flow rates for the output of liquid chromatographs fall within the range of 6ml/min to 0.6ml/min which is approximately 0.1 to 0.01cc/sec. For a cell 18 having a beam diameter of 0.1cm and an optical path $l$ of 0.1cm and a cell cross-sectional area for flow of $3.14 \times 10^{-2}$cm$^2$ the flow rate is approximately 3cm per second to 0.3cm/second. If the modulation frequency is 10 Hertz, then the thermal wavelength $\lambda$ is approximately 0.3cm to 0.03cm.

As liquid flows with velocity V through the laser beam modulated at frequency $\omega$ then it will be temperature modulated as follows at a distance X from the laser beam:

$$T = \sum_{n=1}^{\infty} T_n e^{-\frac{x}{V\tau n}} \sin\left[n\omega\left(t - \frac{x}{v}\right) + O_n\right]$$

where $$\tau_n = \frac{\lambda^2 n}{4\pi^2 \alpha} = \left(\frac{2\pi V}{n\omega}\right)^2 \frac{1}{4\pi^2 \alpha} \; ; \; \lambda_n = \frac{2\pi V}{n\omega} = \frac{\lambda}{n}$$

-continued
$$\tau_n = \frac{V^2}{n^2\omega^2 a}$$

Thus the fundamental $n=1$ propagates the furthest and it decays to $$\frac{1}{e} \text{ at } X = V\tau_1 = \frac{V^3}{\omega^2 a}.$$

Thus to optimize the parameters of the cell the laser beam should be tightly focused to get the thermal absorption power into the fundamental temperature wave. As long as the temperature modulation wavelength is greater than $4r_o$ where $r_o$ is the laser beam radius, then $T_1$ increases as V decreases. Thus for $r_o$ which should be small $\lambda_1$ is approximately $4r_o$ where $\lambda_1$ equals $2\pi V/\omega$ which approximately equals $4r_o$. Also $\omega$ should be made as small as practicable for response time and noise considerations. A frequency in the range of 10 Hertz is preferred.

The major cross-sectional dimension of the detector 22 presented to the flow of liquid should preferably be less than $\lambda_1/2$ for resolution. Also the distance $d$ of the thermal detector 22 to the beam path should be less than about $V^3\omega^2 a$ or the detected signal will be attenuated. For a beam radius $r_o$ of 0.05 cm, a $\lambda_1$ of approximately 0.2cm, and $\omega$ of 62 Rad sec$^{-1}$ or 10 Hertz, then $V$ is approximately 2cm per second and $d$ is approximately 2cm.

The Brewster angle windows 20 are preferably set at angles so that their faces are matched to air on the outside and to the liquid on the inside. This condition is satisfied when $\text{Tan}\theta_1 = n$ window and $\text{Tan}\theta_2 = n$ window/$n$ liquid, where $\theta_1$ is the angle between the window normal and the incident beam ray and $\theta_2$ is equal to the angle between the window normal and the beam ray in the liquid, and $n$ window is the index of refraction in the window material and $n$ liquid is the index of refraction in the liquid sample.

What is claimed is:

1. In a laser infrared absorption apparatus:
cell means for interposing a liquid sample medium to be analyzed in a beam of infrared radiation;
laser means for producing the beam of infrared radiation as a beam of coherent infrared radiation;
means for modulating the intensity of the beam of coherent infrared radiation; and
thermal detection means disposed in heat exchanging relation with the liquid sample and being responsive to the temperature of the liquid sample for detecting the heating effect at the modulation frequency or harmonics thereof in the liquid sample due to the absorption of infrared radiation by the sample from the modulated beam of infrared radiation.

2. The apparatus of claim 1 including, means for directing a flow of the liquid sample through said cell means in the form of a stream.

3. The apparatus of claim 2 wherein said thermal detecting means is disposed downstream of the incident laser beam in the flow of sample liquid through said cell means.

4. The apparatus of claim 3 wherein the major transverse dimension of said thermal detector facing upstream of the direction of liquid flow is less than $\lambda/2$ where $\lambda$ is the modulation thermal wavelength which is equal to $V/f_0$ where $V$ is the fluid flow rate in centimeters per second and $f_0$ is the beam modulation frequency.

5. The apparatus of claim 5 wherein the distance from the thermal detector means to the outer diameter of the infrared beam path in said detector cell is less than $V^3/\omega^2 a$ where $V$ is the velocity of the liquid stream in the detector cell, $\omega$ is the infrared beam modulation frequency in radians, and $a = K/PC$ where $K$ is the thermal conductivity, $P$ is the density and $C$ is the specific heat, respectively, of the liquid sample.

6. The apparatus of claim 3 including a liquid chromatograph having the effluent stream thereof directed through said cell means to form the liquid sample thereof.

7. The apparatus of claim 1 wherein said cell means includes, an infrared permeable window portion through which said laser beam is directed into the liquid sample, and wherein said window portion has one face interfacing with the liquid and a second face interfacing with the medium constituting the surrounds of said cell means, and wherein both faces of said window portion are disposed at Brewster's angle to the laser beam in their respective liquid and surrounding mediums.

8. The apparatus of claim 1 including means for focusing the beam of infrared radiation to a radius, in said detector cell, of less than one-half the modulation thermal wavelength A where $\lambda = V/f_0$ where $V$ is the fluid flow rate in centimeters/second and $f_0$ is the beam modulation frequency.

9. In a method for detecting absorption of infrared radiation by a liquid sample from a laser beam the steps of:
producing a beam of infrared radiation as a beam of coherent infrared radiation;
modulating the intensity of the beam of coherent infrared radiation at a modulation frequency $f_0$;
irradiating a liquid sample medium to be analyzed with the modulation frequency or harmonics thereof due to the absorption of infrared radiation by the sample from the modulated beam of infrared radiation.

10. The method of claim 9 including the step of directing the liquid sample through the beam of infrared radiation in the form of a stream.

11. The method of claim 10 wherein the step of detecting the temperature response in the liquid sample comprises the step of detecting the temperature response of the liquid sample downstream of the incident laser beam path in the flow of sample liquid through the infrared beam.

12. The method of claim 11 wherein the sample liquid comprises the effluent from a liquid chromatograph.

13. The method of claim 9 including the step of, focusing the beam of infrared radiation to a radius in the liquid sample of less than one-half the modulation thermal wavelength $\lambda$ where $\lambda = V/f_0$ where $V$ is the liquid sample flow rate in centimeters/second and $f_0$ is the beam modulation frequency.

14. The method of claim 9 including the step of varying the wavelength of the beam of coherent infrared radiation and detecting the temperature response of the liquid sample as a function of the wavelength of the infrared radiation.

* * * * *